US006936018B2

(12) United States Patent
Chalek

(10) Patent No.: US 6,936,018 B2
(45) Date of Patent: Aug. 30, 2005

(54) REUSABLE/DISPOSABLE THERMAL APPLICATION AND HOLDER DEVICE

(76) Inventor: Matthew J. Chalek, 5828 S. Fulton Way, Greenwood Village, CO (US) 80111

( * ) Notice: Subject to any disclaimer, the term of this patent is extended or adjusted under 35 U.S.C. 154(b) by 0 days.

(21) Appl. No.: 09/955,916

(22) Filed: Sep. 18, 2001

(65) Prior Publication Data

US 2003/0055366 A1 Mar. 20, 2003

(51) Int. Cl.$^7$ ................................................ A61F 5/00
(52) U.S. Cl. ........................... 602/2; 128/876; 607/11; 607/112
(58) Field of Search ................ 602/2; 607/108–112

(56) References Cited

U.S. PATENT DOCUMENTS

| | | | | |
|---|---|---|---|---|
| 4,688,572 A | * | 8/1987 | Hubbard et al. | 128/402 |
| 4,981,135 A | * | 1/1991 | Hardy | 602/2 |
| 5,356,426 A | * | 10/1994 | Delk | 607/112 |
| 5,395,399 A | * | 3/1995 | Rosenwald | 607/111 |
| 5,451,725 A | * | 9/1995 | Goldman | 181/131 |
| 6,149,617 A | * | 11/2000 | McNally et al. | 602/2 |
| 2002/0084295 A1 | * | 7/2002 | Martindale et al. | 224/219 |

OTHER PUBLICATIONS

"Manual for Handling of Applications for Patents, Designs and Trade Marks Throughout the World", *Manual Industrial Property BV*, copyright by Manual Industrial Property BV ISBN 90 71888 010, vol. 2, Germany, pp. 12–18.
"Manual for Handling of Applications for Patents, Designs and Trade Marks Throughout the World", *Manual Industrial Property BV*, copyright by Manual Industrial Property BV ISBN 90 71888 010, vol. 3, Japan, pp. 5–10.

* cited by examiner

*Primary Examiner*—Michael A. Brown
(74) *Attorney, Agent, or Firm*—Kyle W. Rost

(57) ABSTRACT

A therapeutic wrap is disclosed for applying a thermal pad to a human body portion. The wrap includes an elongated flexible strip of disposable and reusable material. The strip has first and second side surfaces, first and second end portions and a mid portion therebetween. A sheet of the disposable and reusable material is secured to the first side surface of the strip to form a pocket which has at least one end opening. The pocket is adapted to receive a prepackaged thermal pad therein through at least one end opening. Finally, a plurality of attachment elements are adapted to releasably secure the first end portion of the strip to any other selected surface portion of the strip in order to conform and secure the strip to a human body portion which requires thermal treatment.

6 Claims, 2 Drawing Sheets

REUSABLE/DISPOSABLE THERMAL APPLICATION AND HOLDER DEVICE

BACKGROUND OF THE INVENTION

1. Field of the Invention

The present invention relates generally to therapeutic wraps for the human body and, more particularly, to devices for applying either reusable or disposable hot or cold packs to differing portions of the human body. Specifically, the present invention is related to therapeutic wraps designed to apply individual hot or cold packs to a wide variety of different portions of the human body which wrap may itself be either disposable or reusable as desired by the user of the wrap.

2. Description of the Prior Art

Physical exercise and, in particular, participation in various athletic activities are currently very popular forms of recreation. Furthermore, physical exercise and athletic activities are entered into by young and old alike, with age being much less a factor these days in limiting one's activities. As a result of such an increase in physical activities by numerous different people of all gender, backgrounds and ages, a wide variety of injuries, both minor and major, have become commonplace. Such injuries occur to joints, muscles and/or limbs in nearly every part or portion of the human body. These injuries are treated in a variety of ways including the use of slings, immobilizing splints, or fluid absorbent materials. In addition, it is common to utilize thermal packs, i.e. either hot packs or cold packs, to alleviate pain, reduce swelling and/or increase blood circulation to the affected body part.

These thermal packs can be one-time-use types of packs, or they may be reusable by heating in a microwave or cooling in a freezer. Examples of such reusable packs include those illustrated in U.S. Pat. Nos. 4,462,224, 4,588,400, 4,756,311, 4,865,012 and 5,150,707. Such thermal packs traditionally have been held in place either by hand, or by swathes of tape or elastic rubberized fabric wrapped around both the thermal pack and the injured body part. The first approach, depending upon the placement of the thermal pad, is uncomfortable, inconvenient or else virtually impossible depending upon the body part to which the thermal pack or pad must be applied. The taping method is awkward at best in that a thermal pack may readily shift position. In the case where the pack must be replaced by a fresh pack in order to maintain the desired temperature, the wrap material must be wrapped and then rewrapped, which is not only time-consuming but may be extremely uncomfortable where adhesive materials are used to secure the pack. Where an elastic fabric bandage is used to secure the pack, the compounded effect of the bandage as it is wrapped around a body and a thermal pack can reduce circulation, or at best may become uncomfortable. Moreover, many people are allergic to adhesives and the rubberized or latex materials used in such tape and elastic wraps.

More recently, specialized thermal packs have been developed which incorporate the thermal pad as a part of an adhesive or wrap material. Examples of such devices are disclosed in U.S. Pat. Nos. 2,573,791, 3,587,578, 3,871,376, 3,889,684, 3,929,131, 5,135,518 and 6,024,761. Other types of specialized thermal packs have been developed that come in a variety of sizes and shapes and are configured to treat a specific body area which is injured. Examples of such body portion specific devices are disclosed in U.S. Pat. No. 5,060,648 (a woman's breast area), U.S. Pat. No. 5,188,103 (the head), U.S. Pat. No. 5,766,235 (the wrist) and U.S. Pat. No. 5,971,947 (tennis elbow). While the specificity of these devices aid in the treatment of injuries, significant difficulties are encountered as one attempts to forecast the various different types of injuries to be incurred and then seeks to have a sufficient variety of specialized thermal packs available to meet these various needs. As a result, if the required specialized device is not available for a specific injury, the injuries are then often treated with rudimentary, makeshift materials which are significantly less effective. This, of course, prevents the most effective treatment at the onset of the injury, which is generally the most crucial time, thus allowing the injured part to worsen as well as to prolong the recovery time.

Instead of injury specific devices, a number of different types of the pack holding devices have been created to contain individual thermal packs or pads as described above. Examples of such devices are disclosed in U.S. Pat. Nos. 4,092,982, 4,676,247, 5,020,711 and 5,697,962. Such thermal pack holders are generally limited in the type of thermal pack utilized, thereby limiting their versatility in application to the specific injury sites. Furthermore, such packs are generally held in place by straps which wrap around the user and are then reattached to themselves. The straps must typically be secured in a particular fashion which further limits the variety of applications possible with such packs. Often, even the simplest modifications of a holder require realignment and twisting of the straps to secure the holder in place. Such general holders are not typically versatile enough to obtain the required configurations. The holder is often not sufficiently secure, and awkward wrapping can be such that the user is caused additional discomfort.

Because injuries can occur to large areas such as shoulders, backs and the like, as easily as to smaller areas such as wrists and elbows, various sized thermal pack holders have been developed. However, the inability of present devices to accommodate both large and small injuries while at the same time conforming to the injury sites for maximum thermal transfer has resulted in the aforementioned proliferation of injury specific thermal packs as well as different sizes of thermal pack holder devices. Moreover, the thermal pack holder devices, especially those designed for use with reusable thermal pads, are relatively complex to manufacture and expensive to purchase and are typically intended for reuse rather than to be disposed of after a single use. However, the cleaning and sanitizing of such reusable holder devices is difficult and messy at best, especially in the everyday household environment.

Therefore, there remains a need for a thermal pack assembly or device which is designed for use with readily available reusable thermal packs, which device is readily adaptable and modifiable for use at any body location to accommodate both large and small injuries without destroying the integrity of the device, and which may be either disposed after a single use or easily cleaned and sanitized for reuse. The present invention satisfies and meets these needs.

SUMMARY OF THE INVENTION

Accordingly, it is one object of the present invention to provide a device for applying thermal packs to portions of the human body.

It is another object of the present invention to provide such thermal pack application devices which are both reusable as well as disposable.

Yet another object of the present invention is to provide a wrap for applying a hot or cold pad to the human body which wrap is flexible and pliable yet is latex-free for allergy protection.

Still another object of the present invention is to provide a thermal pack carrier and application device that is capable of being used to cover a wide variety of human body locations yet permits the replacement of the thermal pack without removal of the applied carrier device.

To achieve the foregoing and other objects and in accordance with the purpose of the present invention, as embodied and broadly described herein, a therapeutic wrap is disclosed for applying a thermal pad to a human body portion. The wrap includes an elongated flexible strip of disposable and reusable material. The strip has first and second side surfaces, first and second end portions and a mid portion therebetween. A sheet of the disposable and reusable material is secured to the first side surface of the strip to form a pocket which has at least one end opening. The pocket is adapted to receive a prepackaged thermal pad therein through at least one end opening. Finally, a plurality of attachment elements are adapted to releasably secure the first end portion of the strip to any other selected surface portion of the strip in order to conform and secure the strip to a human body portion which requires thermal treatment.

In one application of the invention, the elongated flexible strip is pliant in the direction of elongation and is preferably made of latex-free woven cloth of polypropylene fibers. In another application of the invention, the pocket is positioned proximate the second end portion of the strip, while in still another the pocket is positioned proximate the mid portion of the strip.

In yet another application of the invention, the pocket is sized and positioned to enable ready access to at least one end opening thereof to permit replacement of the thermal pad without removing the strip from its applied position about a selected body portion. In one aspect of this application, the attachment elements are in the form of hook and loop type fasteners adapted to selectively secure the strip about a desired body portion. More particularly, the attachment elements are in the form of only the hook-type fastening strips fixed to and extending from the first end portion and which are adapted to removably attach to any selected surface portion of the strip material. In another aspect, the strip may be looped around and secured to itself to form a sleeve wherein the first end portion overlaps the second end portion with the attachment elements selectively varying the diameter of the sleeve by selective attachment to the second surface of the strip.

In yet another application of the invention, an elongated combination disposable and reusable thermal compression wrap is disclosed for applying a thermal pack against a human body portion. The wrap has flexibility in the direction of elongation for assisting in the application and retention thereof against a human body portion. The wrap preferably includes an elongated compression band comprised of flexible woven cloth which is both disposable as well as reusable and is pliant in the direction of elongation. The band has inner and outer surfaces, first and second end portions, and a mid portion intermediate the first and second end portions. A pouch is disposed on the inner surface of the compression band, and the pouch is made from the same flexible woven cloth as the band and has an end opening adapted to permit access to the interior thereof for selective insertion and retrieval of a thermal pack. The band has sufficient pliability to compress the pouch against a selected portion of the human body when applied thereto. A plurality of fastening elements are affixed to and extend outwardly from the first end portion of the band and are adapted to releasably attach to any selected portion of the band's outer surface to enable application of the compression band to any desired portion of the human body

BRIEF DESCRIPTION OF THE DRAWINGS

The accompanying drawings which are incorporated in and form a part of the specification illustrate a preferred embodiments of the present invention and, together with a description, serve to explain the principles of the invention. In the drawings.

DETAILED DESCRIPTION OF THE PREFERRED EMBODIMENTS

Figure 1:
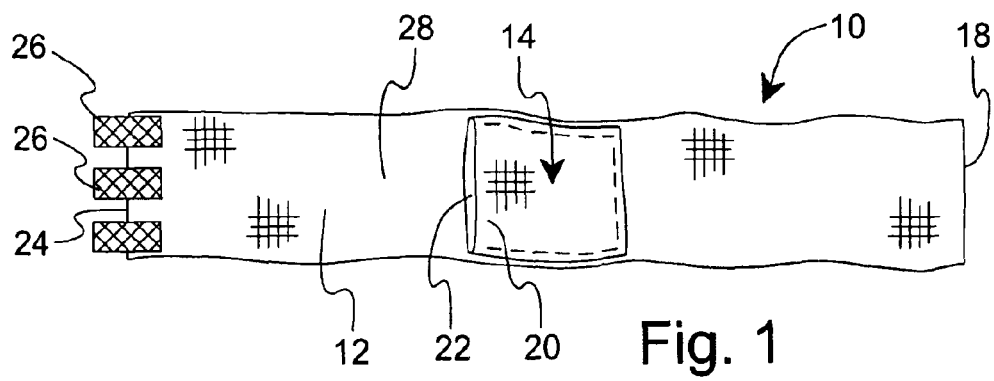
FIG. 1 is a plan view of the inner surface of one embodiment of a thermal application device constructed in accordance with the present invention.
Figure 2:
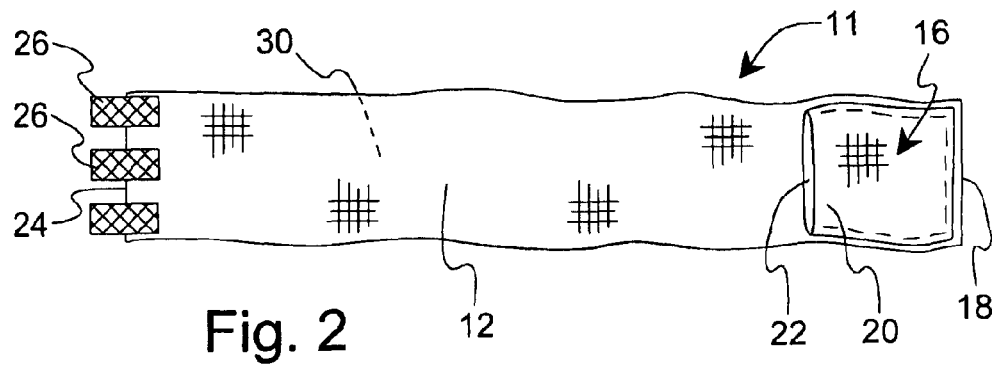
FIG. 2 is a plan view of the inner surface of a second embodiment of a thermal application device constructed in accordance with the present invention.
Figure 3:
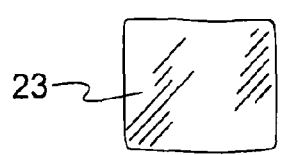
FIG. 3 is a plan view of a typical thermal pack which may be used with the various embodiments of the present invention.

Referring now to FIGS. 1–3, two preferred embodiments of the present invention are illustrated. The present invention is in the form of a wrap 10 that is that is made from a strip 12 which is preferably substantially rectangular in shape and may preferably be up to 20–24 inches in length and approximately 5–6 inches in width. However, the actual dimensions of the strip 12 may be varied as desired or needed. The material of the strip 12 from which the wrap 10 is constructed is preferably a material which is sufficiently flexible to provide a certain amount of elasticity or pliancy in the direction of elongation. A pocket or pouch clement 14 is positioned in the mid portion of the strip 12 midway between the distal ends 18, 24 of the strip 12. As shown in FIG. 1, the compression band or strip 12 is connected to the pocket and provides first and second opposite end portions of the hand or strip 12 that extend away from two opposite edges of the pocket to respective first and second opposite distal ends 24, 18 of the band. In an alternate embodiment as illustrated in FIG. 2, the pouch 16, which is constructed in the same manner as the pouch 14 as described below, is situated proximate one distal end 18 of the strip 12. The pouches 14, 16 are preferably formed by a flap or layer 20 preferably approximately five inches in length and 3.5 inches in width attached preferably along three edges onto the strip 12 so as to form an end opening 22 which provides access to the pouches 14, 16. In preferred form, the layer 20 is attached to the strip 12 by sewing, although any typo of appropriate attachment mechanism may be utilized. A thermal pack 23 can then be readily inserted into the pouches 14, 16 through the end opening 22.

The material of the strip 12 and the pouches 14,16 is preferably latex-free as well as free from any other type of rubberized material so as to avoid allergic reactions by contact with skin. While any number of materials are suitable for the strip 12 and pouches 14, 16, the most preferred is a woven polypropylene fiber. The polypropylene fiber is woven in a manner as to provide the elasticity referenced above and required so that compression force may be administered to a wound as described below. Thus, an additional sheet of the elastic material can be secured to one of the faces of strip 12 to form the pocket. Moreover, the polypropylene fiber is constructed so that if the length of the strip 12 needs to be modified by cutting, the strip 12 will retain its integrity without delaminating or unwinding.

The opposite distal end 24 of the strip 12 includes a plurality of attachment elements 26 which are designed to attach the wrap 12 to a selected body portion of an injured individual. In preferred form, the attachment elements 26 are affixed to the distal end 24 and extend outwardly therefrom. The attachment elements 26 may be any type of known device which may readily attach to the surface of the strip 12 when pressed thereon. In preferred form, the attachment elements 26 are a hook and loop type attachment device and are most preferably be a hook-type portion of a Velcro fastener. In this manner, the fastener 26 will readily secure itself to the strip 12 by simple contact therewith. Thus, each face of strip 12 can be regarded as a fastening means suited to mate with the attachment elements 26. Thus, the wrap 10 can be readily wound about a body portion with the pouch 14, 16 on the inside surface 28 of the strip 12 being pressed against the skin of the injured pony. The fasteners 26 can then be wound over the outer surface 30 and attached thereto at any desired location. As a result of this arrangement, the material of strip 12 must not only be elastic or pliant as described above, but also must be capable of quick and easy attachment to either fasteners 26 yet not stick to the skin surface of an injured party.

Figure 5:
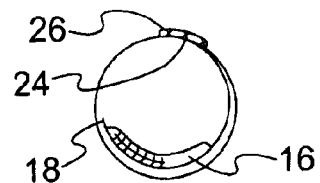
FIG. 5 is an end elevation view of the embodiment of FIG. 4 taken substantially along line 5—5 of FIG. 4.
Figure 4:
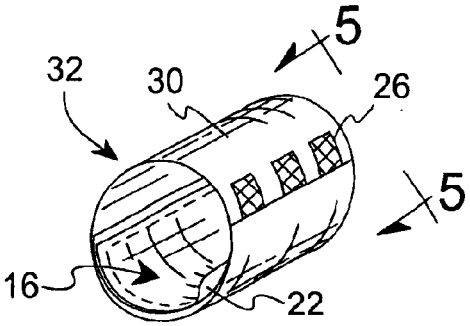
FIG. 4 is a perspective view of the embodiment of FIG. 2 arranged in an alternate form for application to human appendages.
Figure 6:
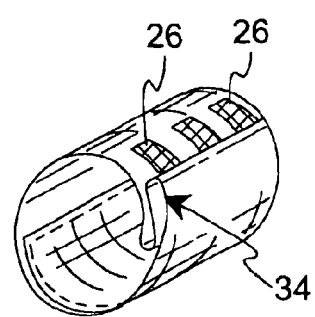
FIG. 6 is a perspective view of the embodiment of FIG. 4 but illustrating an alternate location of the attachment fasteners to vary the diameter of the device.

The embodiments 10, 11 of the invention illustrated in FIGS. 1 and 2 differ simply in the placement of the indicated pouches 14, 16. Another modification of the invention is illustrated in FIGS. 4–6. In this particular modification, the wrap 11 is preferably utilized and wound or looped about itself so that the first distal end 24 overlaps the second distal end 18 to form a sleeve 32. The distal end 18 may be tack stitched to the material 12 to maintain the sleeve size and arrangement as illustrated in FIG. 4. FIG. 6 further shows a band 12 formed into a sleeve wherein first and second end portions of the band are joined together such that attachment elements 26 extend from the junction. In this manner, the sleeve 32 may be readily pulled over an appendage, such as an arm or leg, of an injured party. Once the sleeve 32 is in position, the fasteners 26 may then be moved or drawn over the circumference of the sleeve surface 30 until the sleeve 32 is tightly compressed against the appendage, at which point the fasteners 26 are then secured to the surface 30. Thus, a drawn portion 34 of the sleeve 32 overlaps the remainder of the sleeve depending on the thickness of the appendage over which the sleeve 32 has been positioned.

Figure 9:
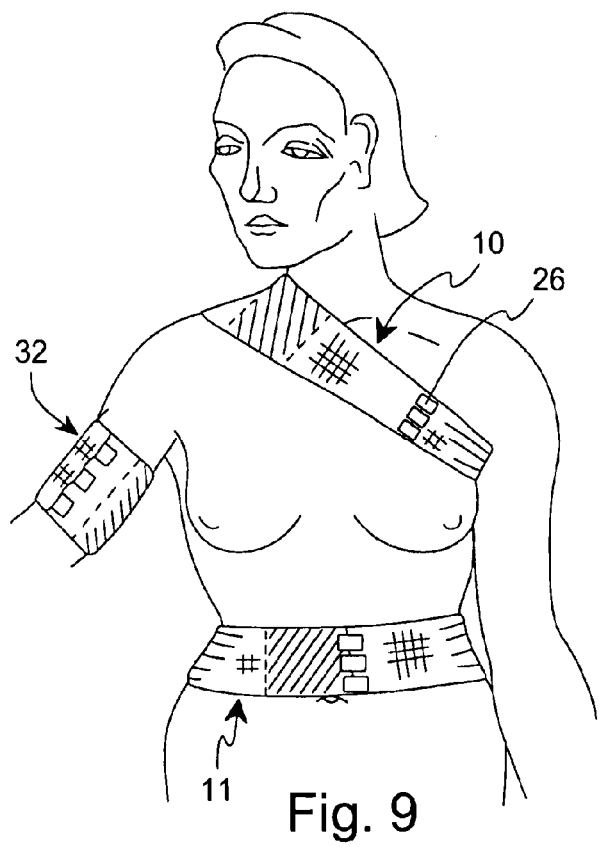
FIG. 9 is a partial front elevation view of several embodiments of the present invention each attached in position about various portions of an individual.
Figure 7:
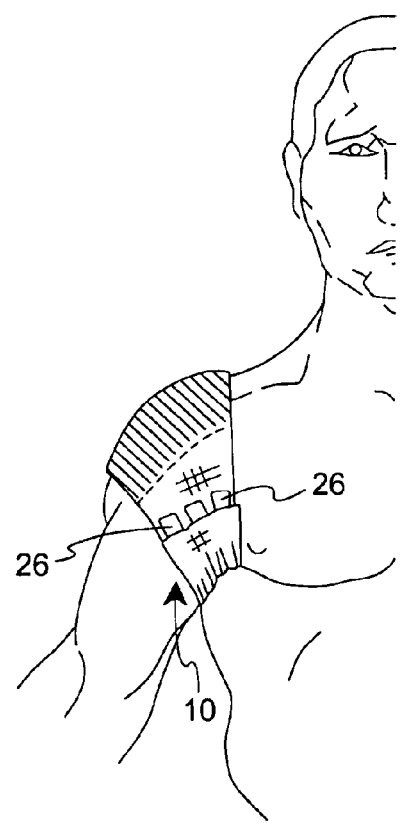
FIG. 7 is a partial front elevation view of an embodiment of the present invention in attached position about the shoulder portion of an individual.
Figure 8:
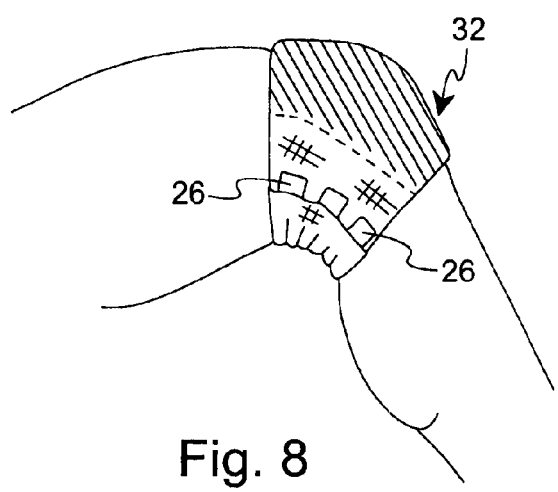
FIG. 8 is a partial side elevation view of an embodiment of the present invention in attached position about the knee of an individual.

Referring now to FIGS. 7–9, the devices 10, 11 and 32 of the present invention are illustrated as being applied to various different portions of a human body. In FIG. 7, the device 10 is illustrated as being wrapped about the shoulder of an individual so that the pouch 14 with its appropriate thermal pad therein is positioned immediately over an injured upper shoulder area. The fasteners 26 secure the device 10 snugly in position so as not only to hold the thermal pad therein over the injured area but as to also apply some compression due to the pliancy or slight elasticity of the material of the strip 12 and the ease of attachment of the fasteners 26 thereto. FIG. 8 illustrates the use of the device 10, 11 or the sleeve 32 over the knee portion of an individual, the fasteners 26 again positioning the sleeve 32 over the injury in a compressed state.

FIG. 9 illustrates several other body locations which could be injured by a person and for which the present invention may be utilized. A collar or lower neck injury can utilize the present invention by placing the device 10 over the injury and under the opposite arm pit as illustrated, the fasteners 26 securing the device 10 in position while compressing the device 10 against the injury. The sleeve 32 may be readily utilized for an upper arm injury as illustrated. Finally, the device 11 of FIG. 2 may be positioned about the lower abdominal area as illustrated in order to utilize the present invention for menstrual cramps or the like. Likewise, the device 11 could be rotated 180 degrees for positioning against the lower back of an individual. It should be understood that as a result of the material selection for the strip 12 of the present invention, the length of strip 12 may be modified and adjusted as necessary by simply cutting away an unneeded portion of the length thereof. The material of the strip 12 will not delaminate or unwind if so cut.

As a result, the present invention permits the placement of either a hot or cold pad onto an injured portion of a human body at essentially any location on the human body, including both large and small muscle groups and joints. Given the width of the pouch 14, 16 relative to the width of the strip 12, the end opening 22 and the interior of the pouch 14, 16 may be accessed even after the device 10, 11 or 32 has been placed on an injured party. Thus, the device 10, 11, 32 does not need to be entirely removed and order to change out the thermal pack as the heat or cold wears off. Inasmuch as there is no latex or rubber included in the strip 12, there is no allergic reaction potential to contact with the skin of a user. However, the slight elasticity and pliancy accommodates adjustability onto an injured body portion as well as permits compression. The material of the strip 12 is both order free and non-sticky inasmuch as adhesive is not used to maintain position of the invention. Due to the thickness of the material utilized in the present invention, more concentrated heat or cold can be applied to the point of injury or pain and may be readily replaced without discomfort to the patient.

A significant aspect of present invention is that the material utilized for the strip 12 is such that the strip 12 is inexpensive to manufacture. Therefore, once the devices 10, 11 or 32 have been utilized and the swelling or pain significantly reduced or eliminated, the device 10, 11 or 32 may be summarily discarded. On the other hand, the material of the strip 12 is also easy to wash and sanitize. This permits the devices 10, 11 or 32 to be reused if one chooses to do so. Consequently, the present invention is both disposable as well as reusable depending upon the needs and choices of the individuals utilizing the same. The material composition and thinness also allows for easy and rapid transfer of heat or cold, as well as insulation, yet prevents burns and retains heat for 16 or more hours.

As can be seen from the above, the present invention provides for a therapeutic wrap adapted for using both hot and cold packs and which allows compression and a customized fit through stretching and unique Velcro positioning. The present invention is not sticky nor greasy, is breathable, latex and adhesive free, and can be cut to size. Moreover, the present invention includes a sleeve-shaped embodiment pre-sewn for joints and smaller appendage muscle groups. The material of the present invention is also very thin and is preferably white in color so that it may be worn discreetly under clothing. The therapeutic wrap of the present invention permits the application of either heat or cold for back aches, sore or stiff backs, arthritis pain and painful joints, sore muscles, stiffness, muscle pain from overuse, minor aches, strains, sprains, menstrual cramp pain and discomfort, and carpal tunnel syndrome pain. It is inexpensive to use, easy to apply and readily adaptable to virtually any portion of the human body requiring treatment. Finally, it may be utilized with any number of readily available heat and cold packs, and is selectively reusable or disposable.

The foregoing description and the illustrative embodiments of the present invention have been described in detail in varying modifications and alternate embodiments. It should be understood, however, that the foregoing description of the present invention is exemplary only, and that the scope of the present invention is to be limited to the claims as interpreted in view of the prior art. Moreover, the invention illustratively disclosed herein suitably may be practiced in the absence of any element which is not specifically disclosed herein.

I claim:

1. A wrap configured as a sleeve that is selectively variable in peripheral size for applying a thermal pad to a variably selected body portion, comprising:

an elongated flexible strip of elastic material having elasticity in the direction of elongation, having first and second end portions joined together such that the strip is configured as a sleeve having an inner face and an outer face, and having a mid-portion between said first and second end portions of said strip;

a sheet of flexible and elastic material secured to a face of said strip at said mid-portion thereof and forming at least one pocket having at least one opening such that said pocket is adapted to receive a prepackaged thermal pad therein through said at least one opening;

an attachment element joined to said sleeve and extending from the outer face of the sleeve in a position enabling the sleeve to be selectively varied in peripheral size by commonly drawing the attachment element and a drawn portion of the sleeve around a remaining portion of the sleeve; and a fastening means extending along the entire surface of said elongated flexible strip of elastic material, sufficiently engageable with said attachment element to secure the drawn portion of the sleeve to any surface portion of the sleeve in drawn position, in a wrapped configuration around a selected body portion.

2. The wrap as claimed in claim 1, wherein:

said attachment element is joined to said sleeve at the junction of said first and second end portions of said elongated flexible strip of elastic material such that the attachment element is enabled to draw the first and second end portions around a remaining portion of the sleeve.

3. An improved wrap suited for applying a thermal pad to any of various different selected body portions of different sizes, wherein the wrap has a pocket defining at least one opening adapting the pocket to receive a prepackaged thermal pad therein through said opening and has a longitudinally elongated flexible and elastic compression band that is elastic in the direction of elongation, having first and second opposite compression band portions extending away from two opposite edges of said pocket to respective first and second distal ends of said band, the band having sufficient length for applying the pocket to a selected body portion by wrapping and applying compression to the body portion, wherein the improvement comprises:

an attachment element carried on a first one of said respective first and second ends of said band distal from said pocket, wherein said attachment element is adapted to releasably fasten to any selected portion of said elastic band to conform and secure the wrap to a selected body portion; and a fastening means extending along the entire surface of said elastic band, engageable with said attachment element to secure the wrap around a selected body portion while permitting any portion of the band, distal from said engaged area, to be severed from the wrap for variably adjusting the fit of the wrap to the size of the selected body portion.

4. The wrap as claimed in claim 3, wherein:

said fastening means comprises first and second faces of said first and second compression band portions, wherein both of said first and second compression band portions are formed of an elastic material that is sufficiently engageable with said attachment element along the entire surface of the first and second faces to establish an engaged area with the attachment element; and said attachment element comprises hook fasteners adapted to engage said elastic material of said fastening means to selectively secure said strip about a desired body portion.

5. The wrap as claimed in claim 4, wherein said attachment element comprises:

a hook-type fastening strip fixed to and extending from said first distal end of said first compression band portion and adapted to removably attach to any selected surface portion of said first and second compression band portions.

6. The wrap as claimed in claim 3, wherein:

said first and second compression band portions are formed of a strip of elastic material having common first and second faces; and said pocket comprises:

a mid-portion of said strip of elastic material providing a first wall of the pocket; and an additional sheet of elastic material secured to one of said faces of said strip;

wherein said mid-portion of the strip and said additional sheet of elastic material together form the pocket.

* * * * *

INTER PARTES REEXAMINATION CERTIFICATE (629th)

United States Patent
Chalek

(10) Number: US 6,936,018 C1
(45) Certificate Issued: Jun. 28, 2013

(54) REUSEABLE/DISPOSABLE THERMAL APPLICATION AND HOLDER DEVICE

(75) Inventor: Matthew J. Chalek, Greenwood Village, CO (US)

(73) Assignee: Heatmax, Inc., Dalton, GA (US)

Reexamination Request:
No. 95/001,311, Mar. 26, 2010

Reexamination Certificate for:
Patent No.: 6,936,018
Issued: Aug. 30, 2005
Appl. No.: 09/955,916
Filed: Sep. 18, 2001

(51) Int. Cl.
*A61F 5/00* (2006.01)
(52) U.S. Cl.
USPC .................. 602/2; 128/876; 607/11; 607/112
(58) Field of Classification Search
None
See application file for complete search history.

(56) References Cited

To view the complete listing of prior art documents cited during the proceeding for Reexamination Control Number 95/001,311, please refer to the USPTO's public Patent Application Information Retrieval (PAIR) system under the Display References tab.

*Primary Examiner* — Cary Wehner

(57) ABSTRACT

A therapeutic wrap is disclosed for applying a thermal pad to a human body portion. The wrap includes an elongated flexible strip of disposable and reusable material. The strip has first and second side surfaces, first and second end portions and a mid portion therebetween. A sheet of the disposable and reusable material is secured to the first side surface of the strip to form a pocket which has at least one end opening. The pocket is adapted to receive a prepackaged thermal pad therein through at least one end opening. Finally, a plurality of attachment elements are adapted to releasably secure the first end portion of the strip to any other selected surface portion of the strip in order to conform and secure the strip to a human body portion which requires thermal treatment.

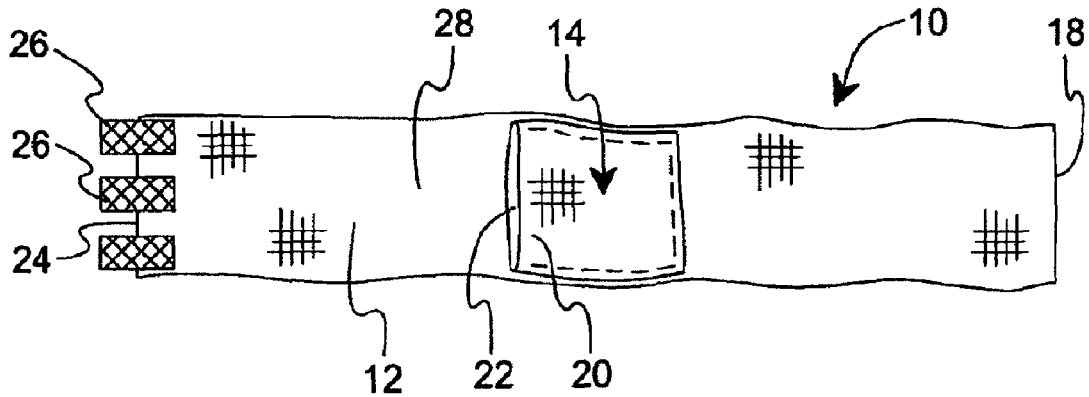

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-6 are cancelled.

* * * * *